United States Patent [19]

Iizuka

[11] Patent Number: 5,046,367

[45] Date of Patent: Sep. 10, 1991

[54] DYNAMIC VISCOELASTICITY MEASUREMENT APPARATUS WITH OUTPUT SIGNAL OFFSET CORRECTION

[75] Inventor: Nobuo Iizuka, Tokyo, Japan

[73] Assignee: Seiko Instruments, Inc., Tokyo, Japan

[21] Appl. No.: 500,289

[22] Filed: Mar. 28, 1990

[30] Foreign Application Priority Data

Mar. 31, 1989 [JP] Japan .................................... 1-82955

[51] Int. Cl.[5] .......................... G01D 1/16; G01D 7/02; G01U 27/72; G01R 33/00
[52] U.S. Cl. ...................................... 73/789; 324/226
[58] Field of Search ............... 324/225, 209, 226, 262; 73/575, 789

[56] References Cited

U.S. PATENT DOCUMENTS 3,374,665  3/1968  Preston .................................. 73/789

Primary Examiner—Walter E. Snow

Attorney, Agent, or Firm—Spensley Horn Jubas & Lubitz

[57] ABSTRACT

An apparatus for dynamic measurement of viscoelasticity of a sample through oscillating displacement thereof. A detector detects oscillating displacement of a sample and produces a corresponding displacement signal having top and bottom peaks and containing an amplitude component due to the oscillating displacement and an offset component due to long-term deformation of the sample. A driver shifts the detector relative to the sample. A measurement circuit measures values of the top and bottom peaks of the displacement signal. A CPU calculates the amount of the offset component according to the measured value of the top and bottom peaks and outputs a compensative signal based on the calculated amount of the offset component to the driver so that the driver shifts the detector relative to the sample according to the compensative signal to cancel the deformation of the sample to thereby remove the offset component from the displacement signal.

6 Claims, 2 Drawing Sheets

DYNAMIC VISCOELASTICITY MEASUREMENT APPARATUS WITH OUTPUT SIGNAL OFFSET CORRECTION

BACKGROUND OF THE INVENTION

The present invention relates to a dynamic viscoelasticity measurement apparatus.

Conventional apparatus of this type is constructed such that the maximum amplitude of the displacement signal of a sample, indicative of the viscoelasticity of the sample, is set to be sufficiently smaller than the measurement range of a peak measurement circuit for measuring the top and bottom peaks of the displacement signal when that signal contains an offset.

The above-noted conventional apparatus has certain drawbacks for example, most of the measurement range of the peak measurement circuit is shared by the offset, which interferes with accurate measurement of the amplitude. In addition, the effective measurement range cannot be enlarged.

SUMMARY OF THE INVENTION

In order to eliminate the above-noted drawbacks of the prior art, an object of the present invention is to remove an offset from an input signal or displacement signal of a sample to enable a peak measurement circuit to measure the amplitude of the input signal, without offset, effectively and with high accuracy.

Another object of the present invention is to utilize a stepping motor to shift a detection mechanism relative to a sample so as to effect expansion of the peak measurement range in the dynamic viscoelasticity measurement apparatus.

In order to achieve the objects of the invention, the dynamic viscoelasticity measurement apparatus is composed of a peak measurement circuit for measuring top and bottom peaks of the displacement signal of a sample, a CPU for receiving an output signal from the measurement circuit and producing a compensative signal according to the received output signal, and a motor driving circuit receptive of the compensative signal for shifting a detection mechanism relative to the sample according to the compensative signal to thereby enable the detection mechanism to produce a compensated displacement signal of the sample, from which any offset is removed.

In operation of the inventive dynamic viscoelasticity measurement apparatus, when the displacement signal is inputted into the peak measurement circuit, this circuit outputs top and bottom peak values to the CPU. The CPU calculates a mean level of the signal from the top and bottom peak values. The CPU then compares the calculated mean level of the displacement signal with a central level of the input or measurement range of the peak measurement circuit to calculate a difference which is an offset of the displacement signal. Then, the CPU outputs a compensative signal effective to cancel that difference. The motor driving circuit operates according to the compensative signal to shift the position of the detection mechanism with respect to the sample to enable the detection mechanism to output a compensated displacement signal of the sample, which is free of any offset, and which is then inputted into the peak measurement circuit. By such operation, even when the position of the sample is shifted relative to the detection mechanism due to thermal expansion or creep of the sample to cause offset in the oscillating displacement signal, such offset can be automatically removed to achieve a highly accurate measurement of the amplitude of the oscillating displacement signal.

DESCRIPTION OF THE PREFERRED EMBODIMENTS

Figure 1:
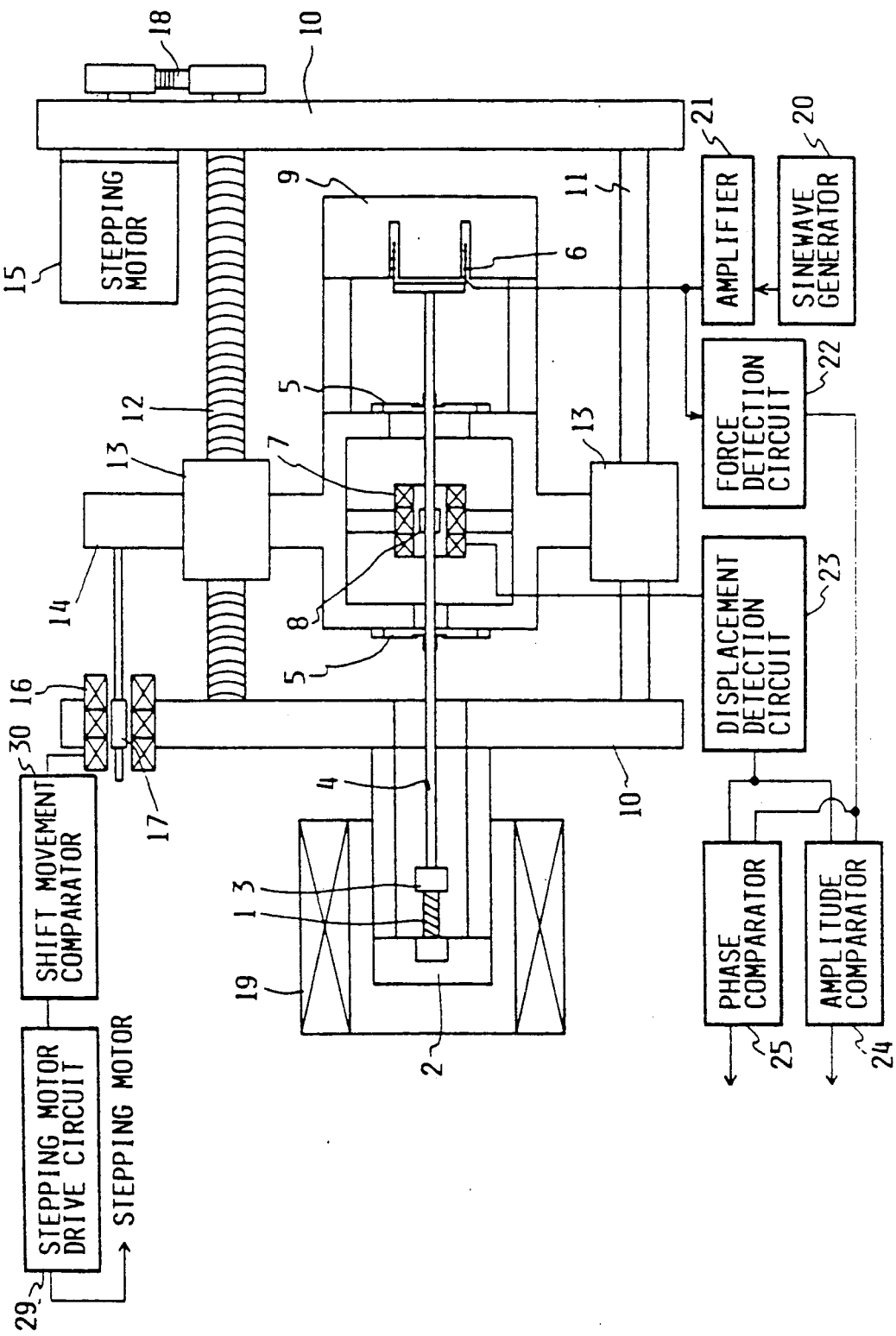
FIG. 1 is a schematic block diagram showing an embodiment of a dynamic viscoelasticity measurement apparatus according to the invention.

Hereinafter, one embodiment of the present invention will be described in detail with reference to the drawings. Referring to FIG. 1, which is a schematic overall block diagram of one embodiment of the dynamic viscoelasticity measurement apparatus according to the present invention, a sample 1 is fixedly held via opposite ends by a sample holder 2 and a sample chuck 3, respectively. The sample chuck 3 is fixed to one end of a detection rod 4. The detection rod 4 is elastically held, in a region intermediate its ends, by a carriage 14 via a pair of detection rod holders 5 each composed of a leaf spring such that the detection rod 4 is able to undergo linear displacement along its longitudinal axis.

A magnetic core 8 is fixed to the intermediate region of the detection rod 4, and a differential transducer 7 in the form of a coil is mounted on the carriage 14, surrounding the core 8, to detect longitudinal displacement of the core 8 due to strain induced in sample 1. A coil 6 is fixed at the other end of detection rod 4, and a magnet 9 is mounted on the carriage 14 to surround the coil 6.

The coil 6 and magnet 9 constitute a force generator for applying a force to the detection rod 4 to induce stress in sample 1, causing a resulting strain in the sample. Further, a furnace 19 is disposed around the sample 1 to place the sample at a defined temperature.

Further, a sine wave generator 20 feeds a sine wave signal to the coil 6 through an amplifier 21 in which the amplitude of the sine wave signal is regulated. The coil 6 cooperates with the magnet 9 in response to the sine wave signal to generate an oscillating or sine wave force effective to cause a corresponding oscillating displacement of the detection rod 4 and the core 8 dependent on the stress-strain characteristic of sample 1.

The output signal from amplifier 21 is further supplied to a force detection circuit 22 to monitor the force associated with the generated sine wave and to output a corresponding force signal. The strain-detection differential transducer 7 detects the oscillating displacement of the core 8 to output a corresponding detection signal to a displacement detection circuit 23 which converts the detection signal into a corresponding oscillating displacement, or strain, signal.

The oscillating force signal from force detection circuit 22 and the oscillating displacement signal from displacement detection circuit 23 are concurrently fed to an amplitude comparator 24 to compare the amplitudes thereof with each other, and are also concurrently fed to a phase comparator 25 to compare the phases thereof with each other. The amplitude comparator 24 outputs a resulting amplitude ratio signal and the phase comparator 25 outputs a resulting phase difference signal. These signals are analyzed to provide an indication of the viscoelasticity of sample 1.

Carriage 14 is engaged with a worm screw or bowl screw 12 and a guide shaft 11 each of which extends through a respective bearing 13 of carriage 14 to undergo a shift movement in the direction of the length of detection rod 4 in both directions according to rotation of screw 12. Screw 12 is driven by means of a stepping motor 15.

When sample 1 undergoes deformation, such as expansion or contraction due to temperature changes, such expansion or contraction is transmitted to detection rod 4 such that core 8 is shifted with respect to strain-detection differential transducer 7. On the other hand, this expansion or contraction can be absorbed at the other end of the detection rod 4 due to a direct current force generated between the drive coil 6 and magnet 9.

As described before, the strain-detection differential transducer 7 detects the displacement of core 8, which may be associated with the relative shift therebetween as well as the oscillating displacement of core 8. The detection result provided by transducer 7 is fed to displacement detection circuit 23, which then outputs the displacement signal, which has an amplitude component corresponding to the oscillating displacement and an offset component corresponding to the shift displacement of core 8.

Figure 2:
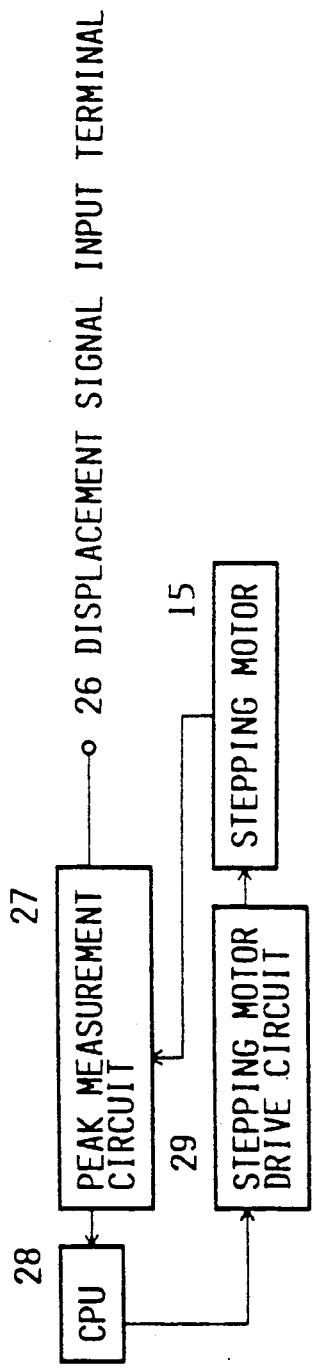
FIG. 2 is a block diagram of an essential portion of the apparatus of FIG. 1.

The displacement signal from detection circuit 23 is applied to a peak measurement circuit 27 and then to a CPU 28, shown in FIG. 2. CPU 28 processes the displacement signal and outputs a control or compensative signal to a stepping motor driving circuit 29, which drives the stepping motor 15 by an amount proportional to the control signal. The rotational torque of the motor 15 is transmitted through a drive belt 18 to rotate screw 12. Thus, the bearings 13 are shifted along screw 12 and shaft 11 in a direction identical to the shifting direction of the core 8 and by a distance identical to the shift displacement of core 8. Since carriage 14 undergoes the linear movement together with the bearings 13, the relative shift between the core 8 and the strain-detection differential transducer 7 can be compensated. As described, the shift movement of carriage 14 is made identical to the shift displacement of core 8.

Another core 17 is fixed to carriage 14, and another differential transducer 16 is fixed to a stationary base frame 10 of the apparatus in opposed relation to the core 17. The differential transducer 16 detects the movement of core 17 to monitor the magnitude of shift movement of carriage 14. The detection signal from differential transducer 16 is inputted into a shift movement comparator 30 which compares the magnitude of the detected actual movement of core 17 with the needed shift amount indicated by the compensative or control signal fed from the CPU.

As described before, the expansion or contraction of sample 1 due to the temperature change, etc., causes a relative shift between differential transducer 7 and core 8. Thus, displacement detection circuit 23 outputs a displacement signal which has an alternating component due to the oscillating displacement of sample 1 and an offset component due to the relative shift between transducer 7 and core 8. As shown in FIG. 2, this displacement signal is inputted into peak measurement circuit 27 through a displacement signal input terminal 26. The peak measurement circuit 27 measures top and bottom peaks of the displacement signal. CPU 28 is connected to the measurement circuit 27 to process the measured results to calculate the offset of the displacement signal so as to output a control or compensative signal according to the calculated offset. The stepping motor driving circuit 29 is connected to CPU 28 for driving stepping motor 15 according to the compensative signal to correct the relative shift between core 8 and differential transducer 7 and thereby eliminate the offset component of the displacement signal.

Figure 3:
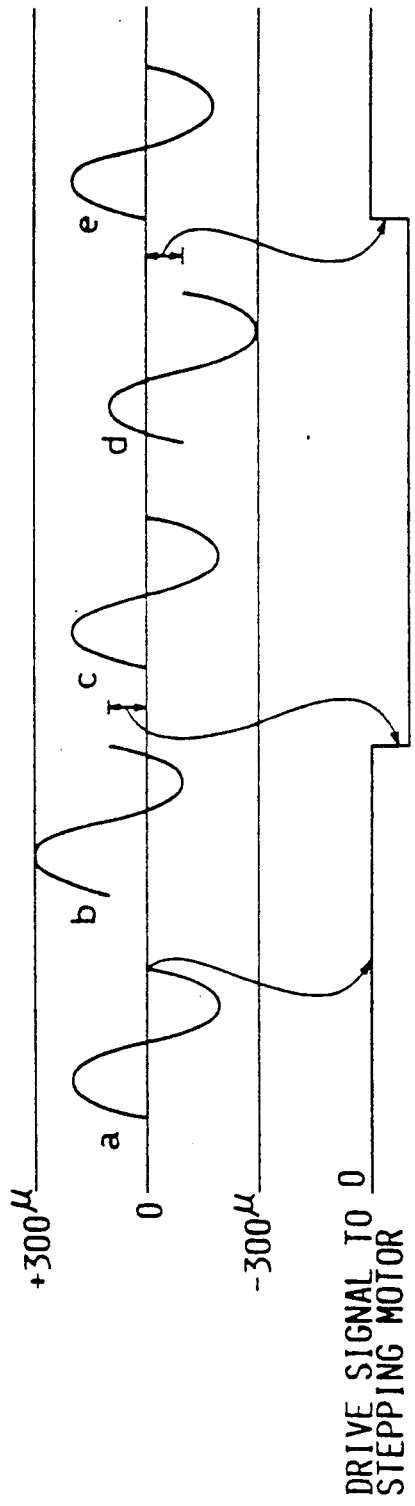
FIG. 3 is a waveform diagram showing the operation of the apparatus according to the invention.

FIG. 3 is a waveform diagram illustrative of the operation of the FIG. 2 circuit. Initially, driving circuit 29 outputs a drive signal representing $0\mu$, effective to hold stepping motor 15 at a rest position. This is the correct position of motor 15 when the displacement signal supplied to input terminal 26 has waveform a. Then, when the displacement signal inputted to input terminal 26 has the waveform b, the peak measurement circuit 27 measures the top and bottom peaks of the inputted displacement signal to determine the top peak value of $+300\mu$ and the bottom peak value of $-100\mu$ in terms of a length unit. The CPU 28 calculates according to the measured values of the top and bottom peaks a mean level of $+100\mu$ indicative of the offset of the inputted displacement signal, and outputs a compensative signal effective to cancel the offset of $+100\mu$ to the stepping motor driving circuit 29. The driving circuit 29 operates in response to the compensative signal to feed an update drive signal of $-100\mu$ effective to drive stepping motor 15 to shift the differential transducer 7 by $-100\mu$. As a result, the offset is canceled so that the compensated displacement signal is inputted into the input terminal 26 in the form of a waveform c.

Then, in this state, in which the stepping motor driving circuit 29 holds the drive signal of $-100\mu$, if the relative shift of $+100\mu$ of rod 4 is returned to the zero value due to a temperature reversal, the displacement signal is inputted into the peak measurement circuit 27 in the form of waveform d instead of waveform a. Thus, the top and bottom peak values of $+100\mu$ and $-300\mu$ are measured and fed to the CPU 28. The CPU 28 calculates the offset of $-100\mu$ according to the measured values of the top and bottom peaks. Then, CPU 28 outputs a new compensative signal, representing $+100\mu$, effective to cancel the offset of $-100\mu$ to the stepping motor driving circuit 29. Consequently, the displacement signal is inputted to the peak measurement circuit 27 in the form of a waveform e to eliminate the offset.

When the displacement signal at the input terminal 26 has an offset due to expansion or creep of sample 1, and even when the offset drifts, the above-described compensative operation is carried out repeatedly to enable the peak measurement circuit 27 to measure the amplitude of the displacement signal with high accuracy while effectively using the measurement range of the measurement apparatus.

As described above, according to the present invention, the offset of the displacement signal can be eliminated so that the peak measurement circuit can measure effectively and accurately the amplitude of the displacement signal precluding the offset. Further, the stepping motor is utilized to broaden the measurement range through the mechanical structural arrangement.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

WHAT IS CLAIMED IS:

1. Apparatus for effecting dynamic measurement of the viscoelasticity of a sample by applying an oscillating deformation force to the sample, said apparatus comprising: detecting means positioned for detecting deformation of the sample relative to a reference deformation value and producing a corresponding deformation signal with maximum and minimum values which are spaced apart by an amount corresponding to the deformation of the sample in response to the oscillating deformation force, the deformation signal having an average value midway between the maximum and minimum values; drive means coupled to said detecting means for displacing said detecting means relative to the sample along the direction of the oscillating deformation force; a measurement circuit connected to said detecting means for determining the maximum and minimum values of the deformation signal relative to the reference value; and calculating means connected for calculating the average value of the deformation signal from the determined values of the maximum and minimum peaks of the deformation signal and for supplying a compensative signal based on the calculated average value to said drive means for causing said drive means to displace said detecting means relative to the sample through a distance for eliminating any difference between the average value of the deformation signal and the deformation signal value associated with the reference deformation value.

2. An apparatus as defined in claim 1 further comprising a stationary frame and wherein said drive means comprise: a carriage carrying said detecting means and supported by said frame for movement along the direction of the oscillating deformation force; a movement transmitting member mounted between said carriage and said frame; and a motor connected for operating said transmitting member in response to the compensative signal supplied by said calculating means.

3. An apparatus as defined in claim 2 wherein said movement transmitting member comprises a screw member and said motor is a stepping motor.

4. An apparatus as defined in claim 3 further comprising a detection rod connectable to the sample for movement in accordance with deformation experienced by the sample, and a position indicating element fixed to said detection rod, and wherein said detecting means comprise a transducer fixed to said carriage for producing the deformation signal as a function of the position of said position indicating element relative to said transducer.

5. An apparatus as defined in claim 2 further comprising a detection rod connectable to the sample for movement in accordance with deformation experienced by the sample, and a position indicating element fixed to said detection rod, and wherein said detecting means comprise a transducer fixed to said carriage for producing the deformation signal as a function of the position of said position indicating element relative to said transducer.

6. An apparatus as defined in claim 1 further comprising a detection rod connectable to the sample for movement in accordance with deformation experienced by the sample, and a position indicating element fixed to said detection rod, and wherein said detecting means comprise a transducer for producing the deformation signal as a function of the position of said position indicating element relative to said transducer.

* * * * *